United States Patent [19]

Netterville et al.

[11] Patent Number: 5,531,752
[45] Date of Patent: Jul. 2, 1996

[54] VOCAL CORD MEDIALIZATION TOOL

[75] Inventors: James L. Netterville, Nashville, Tenn.;
James B. Hissong, Jacksonville, Fla.

[73] Assignee: Xomed, Inc., Jacksonville, Fla.

[21] Appl. No.: 10,914

[22] Filed: Jan. 29, 1993

Related U.S. Application Data

[62] Division of Ser. No. 763,390, Sep. 20, 1991, Pat. No. 5,201,765.

[51] Int. Cl.⁶ .................................................. A61B 17/58
[52] U.S. Cl. ............................ 606/99; 623/9; 128/774
[58] Field of Search ........................... D10/61, 64, 70; D24/133, 155; 128/774, 777; 623/9, 11; 33/417, 421, 423, 511, 515, 555, 514.2; 606/99, 102

[56] References Cited

U.S. PATENT DOCUMENTS

| 1,845,829 | 2/1932 | Carnal | 16/86 A |
| 3,706,112 | 12/1972 | Newell | 16/86 A |
| 4,881,293 | 11/1989 | Reynolds | 16/86 A |
| 4,938,234 | 7/1990 | Capriotti | 623/10 |
| 5,030,232 | 7/1991 | Pham | 623/10 |

FOREIGN PATENT DOCUMENTS 453186  10/1991  European Pat. Off. ................ 623/9

*Primary Examiner*—Robert A. H. Clarke
*Attorney, Agent, or Firm*—Gipple & Hale; John S. Hale

[57] ABSTRACT

A vocal cord medialization prosthesis includes a preformed and presized vocal cord engagement member. The engagement member has a base surface and an engagement surface that is inclined a predetermined amount with respect to the base surface. Measurement indicia is provided on the engagement member to indicate elevation of the engagement surface at predetermined points along the prosthesis. A vocal cord medialization tool is used to measure displacement of a vocal cord to an optimum phonation and breathing position before insertion of the prosthesis. The medialization tool provides measurements that correspond to sizing indicia on the prosthesis. The prosthesis can thus be trimmed to eliminate elevations that are unnecessary for obtaining optimum positioning of a vocal cord. One embodiment of the medialization tool also includes provision for measuring the thickness of a thyroid cartilage.

9 Claims, 3 Drawing Sheets

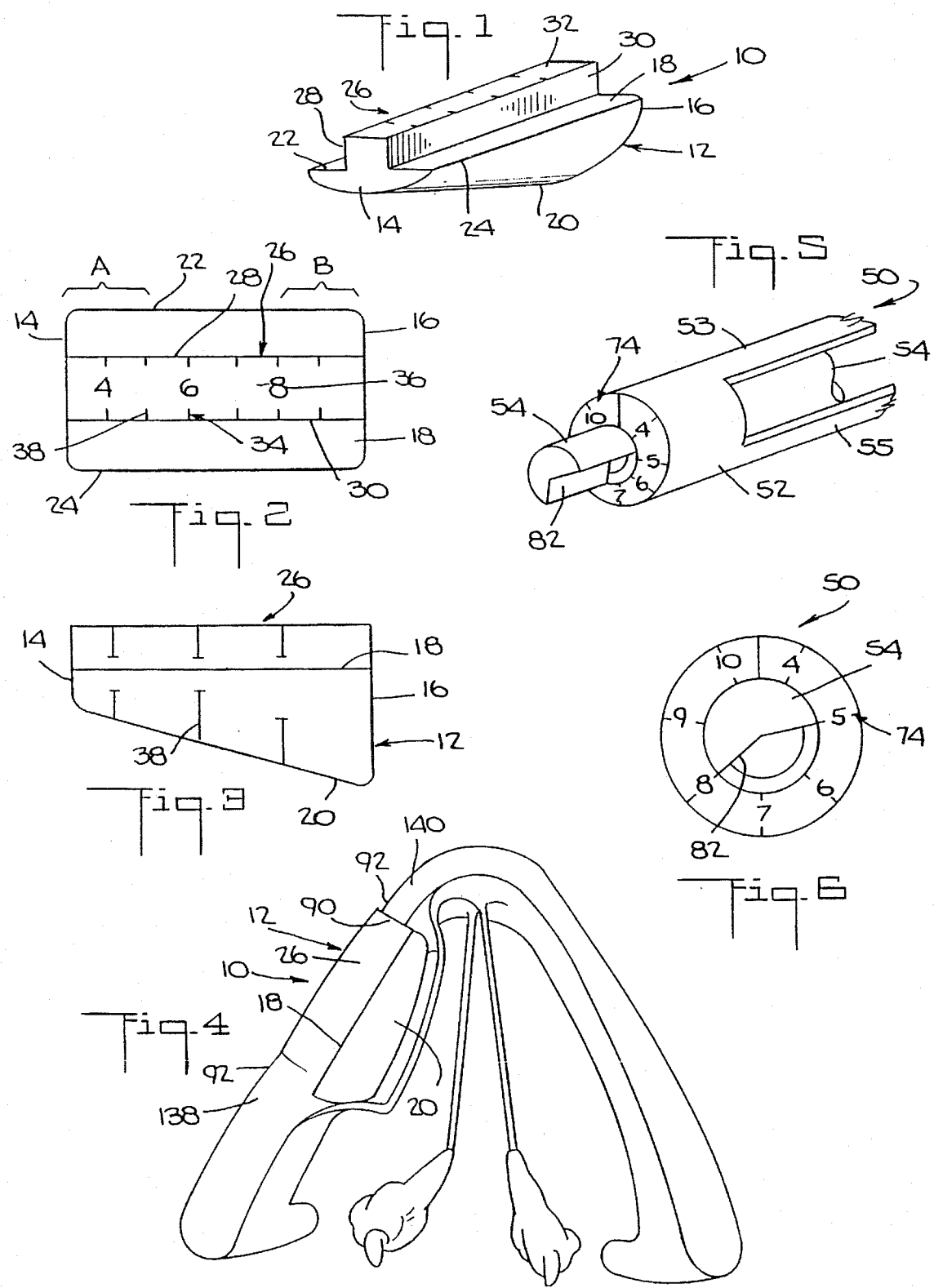

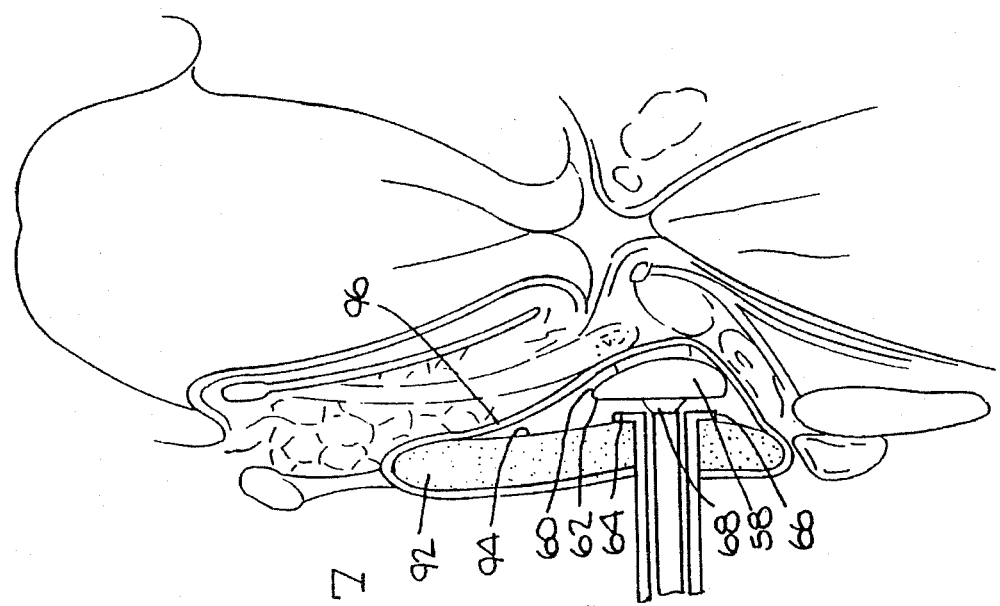
Fig. 7
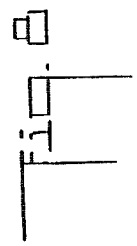
Fig. 8
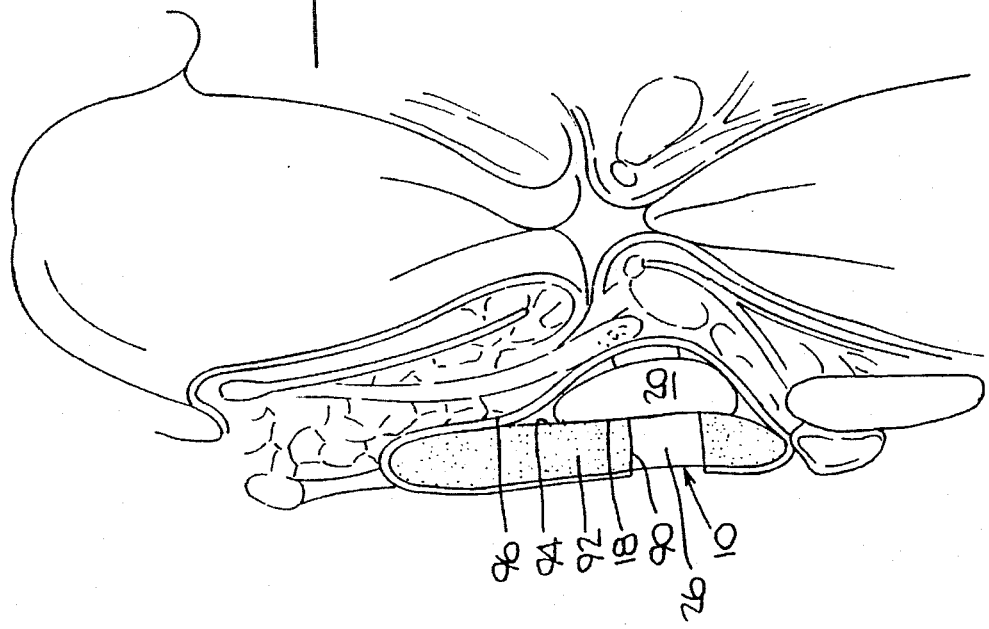

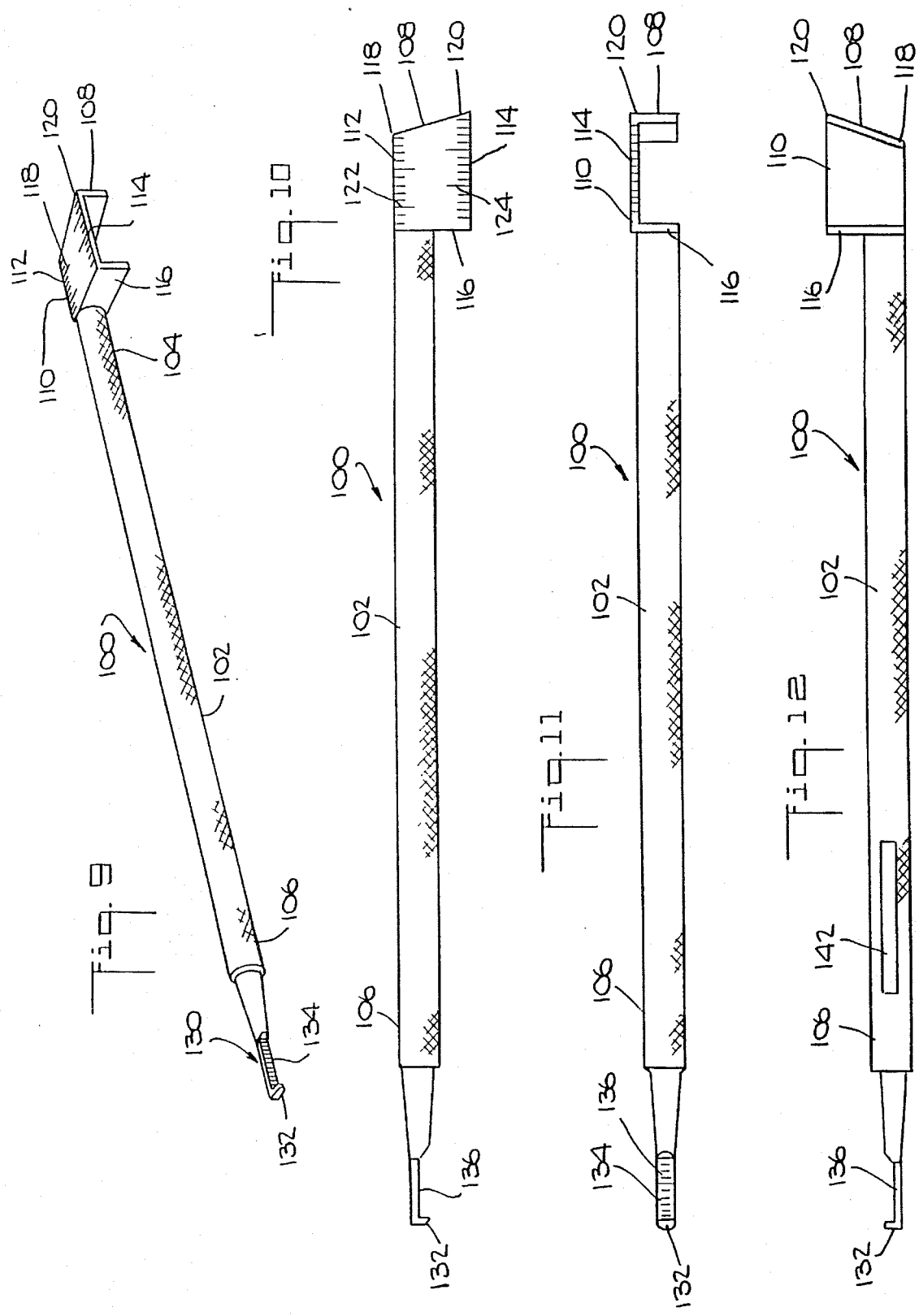

VOCAL CORD MEDIALIZATION TOOL

This is a divisional application of application Ser. No. 07/763,390, filed Sep. 20, 1991 now U.S. Pat. No. 5,201,765.

BACKGROUND OF THE INVENTION

This invention relates to prosthetic devices for medializing a vocal cord, and more particularly to a preformed and presized prosthetic device for obtaining optimum displacement of a vocal cord to correct dysphonia due to vocal cord dysfunction.

Vocal cords or vocal folds normally undergo dynamic movement between a relatively closed phonation position and a relatively open breathing position to allow an individual to speak and breathe. Phonation generally occurs when the vocal cords are in their relatively closed position, which obstructs the flow of air. Thus normal breathing is difficult when phonation occurs. Breathing is facilitated when phonation is interrupted to enable the vocal cords to move to their relatively open position. Vocal cord dysfunction or dysphonia usually occurs when one of the vocal cords is paralyzed and recedes into a slightly divergent open position resulting in reduced phonation capability.

In one known treatment of vocal cord dysfunction, a laryngoplasty is performed wherein an implant such as a silicone block is installed between the thyroid cartilage and the paralyzed vocal cord to medialize the vocal cord. The shaping and sizing of the implant is usually a manual procedure performed by the surgeon on an empirical basis who custom forms the prosthesis based on an estimate of the amount of medialization needed by the patient.

A preliminary version of the implant is inserted between the vocal cord and the thyroid cartilage and the patient's phonation ability is evaluated. If there is a need for further medialization the prosthesis is removed and resized and/or reshaped and again inserted between the vocal cord and the thyroid cartilage for further evaluation of the patient's phonation ability.

Often two or more insertions and modifications of an implant are made in this manner in order to obtain the desired medialization.

A problem that arises in connection with each insertion and subsequent removal of an implant is that the patient can suffer trauma and tissue edema. Swelling of tissue often leads to a false determination of optimum size for an implant. For example, when tissue edema recedes it may become apparent that there is an undercorrection of the vocal cord medialization because the tissue edema caused a false reading of implant requirements. Thus one of the greatest difficulties with current laryngoplasty techniques is that an implant must be repeatedly inserted in a patient and modified in accordance with empirical assessments of required medialization.

It is thus desirable to provide a preformed and presized prosthesis for medializing a vocal cord and a tool for displacing a vocal cord to an optimal phonation position and measuring the amount of displacement to permit use of the presized prosthesis.

OBJECTS AND SUMMARY OF THE INVENTION

Among the several objects of the invention may be noted the provision of a novel prosthesis for medializing a vocal cord, a novel prosthesis for medializing a vocal cord that is preformed to a predetermined size, a novel prosthesis for medializing a vocal cord that is presized to provide optimum medialization displacement of a vocal cord from a thyroid cartilage, a novel prosthesis for medializing a vocal cord that has different sizes and which permits easy trimming to a desired size, a novel vocal cord medialization tool which displaces a vocal cord from a thyroid cartilage to a desired medialization position, a novel vocal cord medialization tool which medializes the vocal cord and permits measurement of the amount of medialization obtained, a novel vocal cord medialization tool which permits measurement of the thickness of the thyroid cartilage as well as medialization of the vocal cord and measurement of the amount of vocal cord medialization, and a method of medializing a vocal cord.

Other objects and features of the invention will be in part apparent and in part pointed out hereinafter.

In accordance with the invention, the vocal cord medialization prosthesis includes a preformed engagement member that is presized with a dimensional scale that corresponds to different dimensions on the prosthesis. The dimensional scale indicates elevation of an engagement surface of the prosthesis from a base surface at various points along the prosthesis.

A vocal cord medialization tool that can be used in conjunction with the prosthesis is shaped similarly to the prosthesis. The vocal cord tool provides measurements of optimum vocal cord displacement from a thyroid cartilage before insertion of the prosthesis. Dimensions on the prosthesis correspond to the measurement of vocal cord medialization position provided by the tool which establishes the exact size of prosthesis needed for vocal cord medialization.

The preformed prosthesis, in one embodiment, is longer than necessary, and is trimmed to eliminate one or more longitudinal sections that are unnecessary. The resulting trimmed prosthesis, when installed, will thus move the vocal cord away from the thyroid cartilage to the optimum phonation/breathing position (medialization position) determined by the vocal cord measuring tool.

The vocal cord medialization tool, in one embodiment, includes dimensions at the same end of the tool that engages a vocal cord during measurement of optimum vocal cord displacement. In another embodiment of the vocal cord medialization tool, a dimensional scale is provided at an opposite end of the tool from that which engages a vocal cord during measurement of vocal cord medialization.

Provision is also made in one of the vocal cord medialization tools for measuring the thickness of thyroid cartilage at the area where a prosthesis is to be installed.

The invention accordingly comprises the constructions and method hereinafter described, the scope of the invention being indicated in the claims.

DESCRIPTION OF THE DRAWINGS

In the accompanying drawings,

FIG. 1 is a simplified perspective view of a prosthetic device for medializing a vocal cord incorporating one embodiment of the invention;

FIG. 2 is a bottom view thereof;

FIG. 3 is a side view thereof;

FIG. 4 is a simplified side view thereof in installed position;

FIG. 5 is a fragmentary perspective view of a vocal cord medialization tool;

FIG. 6 is an end view thereof;

FIG. 7 is a simplified side view of the vocal cord medialization tool as used to measure the medialization position of a vocal cord;

FIG. 8 is a simplified end view of the vocal cord medialization prosthesis in an installed position;

FIG. 9 is a simplified perspective view of another embodiment of a vocal cord medialization tool;

FIG. 10 is a top plan view thereof;

FIG. 11 is a side elevation thereof; and,

FIG. 12 is a bottom view thereof.

Corresponding reference characters indicate corresponding parts throughout the several views of the drawings.

DETAILED DESCRIPTION OF THE INVENTION

A vocal cord prosthesis incorporating one embodiment of the invention is generally indicated by the reference number 10 in FIG. 1.

The prosthesis 10, which is preferably formed of silicone, comprises an elongated engagement member 12 that is elongated in a longitudinal direction. The engagement member 12 has longitudinally spaced opposite end portions 14 and 16, a base surface 18 and a vocal cord engagement surface 20 extending from the base surface 18.

The engagement member 12 further includes laterally spaced edge portions 22 and 24 where the base 18 and the vocal cord engagement surface 20 intersect. An elongated tab portion 26 projects from the base surface 18 and is coextensive with the base surface 18 in the longitudinal direction. The tab portion 26 includes side wall portions 28 and 30 and a floor portion 32 that is provided with indicia 34 such as numbers and a dimensional scale which can correspond to millimeters, for example.

The vocal cord engagement surface 20 is inclined with respect to the base surface 18 a predetermined amount, preferably 15.6°. The vocal cord engagement surface 20 is curved in a lateral direction from the edge portion 22 to the edge portion 24. The maximum distance between the vocal cord engagement surface 20 and the base surface 18 is defined as the elevation of the engagement surface.

The indicia 34 includes numbers 36 and scale markings 38 that represent the elevation of the engagement surface 20 from the base surface 18. If desired the scale markings 38 can be extended along the engagement surface 20 such as shown in FIG. 3.

Thus the numbers 4, 6 and 8 at indicia 34 are located on the prosthesis 10 at the point where the engagement surface 20 is elevated 4 mm., 6 mm. and 8 mm. from the base surface 18. The scale markings 38, which are not numbered, indicate intermediate numbers 5, 7 and 9 where the engagement surface 20 is elevated 5, 7 and 9 mm. from the base surface 18. The end portion 14 corresponds to an elevation of 3 mm. and the end portion 16 corresponds to an elevation of 10 mm.

A vocal cord medialization measurement tool which can be used in combination with the prosthesis 10 is generally indicated by the reference number 50 in FIGS. 5, 6 and 7. The tool 50 includes a sleeve portion 52 and a stem portion 54 protractible and retractable in the sleeve 52 by threads 56 provided on a peripheral portion of the stem 54 for engagement with complementary threads in the sleeve 52. The sleeve 52 and stem 54 can be formed of a suitable material such as stainless steel. The sleeve 52 has longitudinally extending spaced leg portions 53 and 55.

Referring to FIG. 7, one end portion of the stem 54 is provided with a vocal cord engagement member 58 preferably formed of silicone. The engagement member 58 has a vocal cord engagement surface 60 and a base surface 62 and is joined to an end of the stem 54 by a suitable known joint 68 that permits rotation of the stem 54 with respect to the engagement member 58. The engagement surface 60 is inclined with respect to the base surface 62 at approximately the same angle as the engagement surface 20 is inclined with respect to the base surface 18 of the prosthesis 10. The leg portions 53 and 55 are provided with upper and lower flanges 64 and 66 that project radially away from the free ends of the leg portions 53 and 55.

Referring to FIGS. 5 and 6, an outside end of the sleeve 52 is provided with indicia means 74 that include numbers 4 through 10 radially spaced from each other. Referring to FIG. 7, a size indicator 80 is formed on the stem 54 proximate the indicia 74. The size indicator 80 can be in the form of a dial that spans a predetermined size range such as 3 mm. Alternatively, the size indicator 80 can be in the form of a V-shaped recess 82 as shown in FIGS. 5 and 6, which spans a similar 3 mm. size range.

In using the prosthesis 10, a measurement of vocal cord medialization is initially taken using the medialization tool 50. A window or opening 90 (FIG. 8) is cut into the thyroid cartilage 92 to permit insertion of the tool 50 and ultimate insertion of the prosthesis 10.

The tool 50 is preliminarily set to a position wherein the vocal cord engagement member 58 is at its closest proximity to the flanges 64 and 66 of the leg portions 53 and 55. The vocal cord engagement member 58 and the flanges 64 and 66 are passed through the window opening 90 in the manner shown in FIG. 7, such that the flanges 64 and 66 engage an inside surface 94 of the thyroid cartilage 92 and the engagement surface 60 of the engagement member 58 engages a vocal cord 96. To facilitate such insertion the leg portions 53 and 55 can be squeezed together against the stem portion 54.

With the vocal cord medialization tool 50 in the position shown in FIG. 7, a patient can attempt phonation. During phonation the stem 54 is threaded in the sleeve 52 to protract the engagement member 58 and displace the vocal cord 96 away from the thyroid cartilage 92 to an optimum phonation position that is determined by the physician. Rotation of the stem 54 permits protraction of the engagement member 58 from the sleeve 52 without causing rotation of the engagement member 58. It should be noted that the optimum phonation position is essentially a compromise position of the vocal cord 96 that permits breathing as well as phonation.

At the optimum phonation or medialization position, the size indicator 82 in FIGS. 5 and 6 (or 80 in FIG. 7) will indicate the size elevation range of the prosthesis 10 that will replicate the medialization position of the vocal cord 96 by the vocal cord medialization tool 50.

Thus for example, if the vocal cord medialization tool 50 indicates a size range of 5 mm. to 8 mm. as shown in FIG. 6, the prosthesis 10 is trimmed to eliminate the sections indicated at reference letters A and B in FIG. 2. The tool 50 is adjusted back to its preliminary adjustment position and removed from the window opening 90.

Since the prosthesis 10 is formed of a trimmable material such as silicone, the portion of the prosthesis 10 which is less than 5 mm. is easily trimmed off and the portion of the prosthesis 10 which is greater than 8 mm. is also easily trimmed off.

The prosthesis 10 is inserted through the window opening 90 in the thyroid cartilage 92 in the manner shown in FIG. 8, such that the engagement surface 20 of the engagement member 12 bears against the vocal cord 96 and the base surface 18 of the engagement member 12 bears against the inside surface 94 of the thyroid cartilage 92. The tab portion 26 projects into the window opening 90 from the inside surface 94 of the thyroid cartilage 92. Pressure between the thyroid cartilage 92 and the vocal cord 96 maintains the prosthesis 10 in its implanted position.

In this manner, a patient is measured for optimum vocal cord medialization using the tool 50 and then fitted with the prosthesis 10 to obtain optimum medialization. Any edema that may occur after the measurement procedure will not affect vocal cord medialization since the prosthesis 10 is sized to correspond to the measurement of optimum phonation position provided by the tool 50.

Thus the prosthesis 10 for medializing a vocal cord is sized to correspond exactly to the measurements indicated by the vocal cord medialization tool 50, thereby permitting use of the preformed prosthesis having a predetermined size.

If desired, pretrimmed prostheses can be provided in selected different sizes to correspond to measurements indicated by the medialization tool 50.

Another embodiment of a vocal cord medialization tool is generally indicated by the reference number 100 in FIG. 9. The tool 100 has an elongated stem portion 102 that can be formed of a suitable material such as stainless steel, and includes end portions 104 and 106. A vocal cord engagement surface 108 is joined to the stem portion 102 proximate the end portion 104. The engagement surface 108 is inclined with respect to the direction of elongation of the stem portion 102. A size indicator 110 joins the vocal cord engagement surface 108 to the end portion 104 of the stem 102. The size indicator 110 includes indicia such as 112 and 114 (FIG. 10) for indicating the distance between the engagement surface 108 and a thyroid cartilage 92. The size indicator 110 further includes an end portion 116 adjoining the end portion 104 of the stem 102. The end portion 116 is approximately perpendicular to the direction of elongation of the stem portion 102.

The indicia 112 which preferably includes scale lines corresponding to millimeters, has a point 118 of minimum elevation from a thyroid cartilage at the engagement surface 108. The indicia 114, which also includes a millimeter scale, has a point 120 of maximum elevation at the vocal cord engagement surface 108. The indicia 112 can include bold lines 122 at every fifth millimeter to facilitate measurements using the indicia 112. Correspondingly, the indicia 114 includes bold lines 124 at every fifth millimeter to facilitate measurements using the indicia 114.

Although the end portion 116 is shown to depend from the size indicator 110 an amount that is substantially equivalent to the amount that the engagement surface 108 depends from the size indicator 110, such dependency can be omitted. Thus the engagement surface 108 can be reduced to a rounded edge of the size indicator 110 and the end portion 116 can be reduced to an opposite edge of the size indicator 110.

It should be noted that the inclination of the engagement surface 108 with respect to the end portion 116 corresponds to the inclination of the engagement surface 20 of the prosthesis 10 with respect to the base surface 18. The tool 100 further includes a second size indicator 130 at the end portion 106 of the stem for measuring thyroid cartilage thickness. The size indicator 130 includes a thyroid cartilage engaging finger 132 and indicia 134 provided at a surface 136 of the size indicator 130. The indicia 134 includes a scale of dimensional lines which can correspond to millimeters. A bold line or recess can be formed in the surface 136 at the 5 mm. point to facilitate visualization of measurements made along the indicia 134.

The tool 100 permits measurements of thyroid cartilage thickness as well as displacement of a vocal cord from a thyroid cartilage in ascertaining optimum vocal cord position for vocal cord medialization.

For example, referring to FIG. 4, it will be seen that the thyroid cartilage 92 is relatively thick at a location indicated by reference number 138 at one longitudinal end of the prosthesis 10, and relatively thin at a location 140 at an opposite end of the prosthesis 10. Since the thyroid cartilage 92 is not of uniform thickness, it is often helpful to ascertain the thickness of the cartilage at the location 138 as well as the location 140. This thickness can be measured by inserting the size indicator 130 in the window opening 90 of the cartilage 92 such that the cartilage engaging finger 132 engages the inside surface 94 of the thyroid cartilage at the cartilage location 138. Measurement of the cartilage thickness at the location 138 can be read from the scale of indicia 134. Similarly, the thickness of the cartilage 92 at the location 140 can be read by positioning the finger 132 of the size indicator 130 at the location 140.

After the cartilage thickness is measured at the locations 138 and 140, and at any other points at the window opening 90, the tool 100 is repositioned to permit the engagement surface 108 to pass through the window opening 90 for engagement with the vocal cord 96 (not shown). The size indicator 110 is passed through the window opening 90 to dispose the engagement surface 108 against the vocal cord 96 (not shown).

When the vocal cord 96 is displaced by the engagement surface 136 to a position of optimum phonation and breathing, the indicia 112 and 114 are observed for measurement of such displacement. For example, a measurement is made on the indicia 112 of the distance between the point of minimum elevation 118 from the inside surface 94 of the thyroid cartilage 92. In addition, a further measurement is made on the indicia 114 of the distance between the point of maximum elevation 120 from the inside surface 94 of the thyroid cartilage 92. A minimum elevation reading is thus made from the indicia 112 and a maximum elevation reading is made from the indicia 114. Based on these readings, the prosthesis 10 can be trimmed to replicate the minimum and maximum elevation measurements determined by the medialization tool 100.

Portions of the prosthesis 10 which contain an elevation greater than the measured maximum elevation can be removed or trimmed away. Similarly, portions of the prosthesis 10 which have an elevation less than the minimum elevation measurement can be removed or trimmed away. The prosthesis 10 with the trimmed away portions is then inserted through the window opening 90 such that the minimum elevation end of the prosthesis corresponds with the relatively thin section of the thyroid cartilage 138 and the maximum elevation portion of the prosthesis 10 corresponds with the relatively thick portion of cartilage 140 as shown in FIG. 4.

It will be noted that the finger 132 of the size indicator 130 is offset by approximately 90° from the engagement surface 108. A flattened portion 142 can be provided on the stem 102 to facilitate proper orientation of the engagement surface 108.

Some advantages of the invention evident from the foregoing description include a prosthesis for medialization of a vocal cord that is preformed to a predetermined size to facilitate location of a vocal cord in its optimum phonation and breathing position. A further advantage is that the prosthesis is preformed with a predetermined inclination or gradation of elevation. Another advantage is that a medialization tool has an inclination corresponding to the inclination of the prosthesis and a measurement scale corresponding to the indicia provided on the prosthesis. The prosthesis can thus be trimmed to the exact size indicated during a measurement of vocal cord displacement by the medialization tool.

Still another advantage is that the medialization tool eliminates guesswork and empirical reinsertions of an implant in determining the correct size of a prosthesis. The medialization tool and the preformed, presized implant reduce the likelihood of undercorrection or overcorrection due to edema of the tissues because of multiple insertions of an implant. Since the measurement of optimum vocal cord displacement is made with the medialization tool, subsequent edema will not affect the selected size of the prosthesis. Thus the possibility of undercorrection of vocal cord position due to edema is minimized.

In view of the above, it will be seen that the several objects of the invention are achieved and other advantageous results attained.

As various changes can be made in the above constructions and method without departing from the scope of the invention, it is intended that all matter contained in the above description or shown in the accompanying drawings shall be interpreted as illustrative and not in a limiting sense.

What is claimed is:

1. A vocal cord medialization tool comprising,
   a) an elongated stem having opposite longitudinal end portions,
   b) a vocal cord engagement surface proximate one of said longitudinal end portions for displacing a vocal cord from a thyroid cartilage,
   c) a thyroid cartilage engaging surface proximate said one of said longitudinal end portions and spaced from said vocal cord engagement surface,
   d) said vocal cord engagement surface having laterally spaced end portions, said vocal cord engagement surface projecting away from said thyroid cartilage engaging surface and having a first range of steadily increasing elevation from said thyroid cartilage engaging surface, from a minimum elevation at one said lateral end portion of said vocal cord engagement surface to a maximum elevation at the other said lateral end portion of said vocal cord engagement surface, and
   e) a first size indicator on said stem for indicating the elevation of said vocal cord engagement surface from said thyroid cartilage engaging surface in a longitudinal direction between said minimum and said maximum elevations.

2. The tool as claimed in claim 1 wherein said stem is elongated in a first direction, and said vocal cord engagement surface has a predetermined inclination with respect to said first direction.

3. The tool as claimed in claim 2 wherein said tool further includes a sleeve having opposite end portions corresponding to the opposite longitudinal end portions of said stem, and said thyroid cartilage engaging surface is provided at one end portion of said sleeve corresponding to said one longitudinal end portion of said stem.

4. The tool as claimed in claim 3 wherein said first size indicator is provided at an opposite longitudinal end portion of said stem, said tool further including indicia means at the opposite end of said sleeve corresponding to the opposite end of said stem, for cooperation with said first size indicator.

5. The tool as claimed in claim 4 wherein said first size indicator includes a dial for indicating a size range on said indicia means.

6. The tool as claimed in claim 5 wherein said dial includes a recess in said stem.

7. The tool as claimed in claim 5 wherein said dial projects from said stem.

8. The tool as claimed in claim 2 further including a sleeve, said stem being protractible and retractable from said sleeve to protract and retract said vocal cord engagement surface.

9. The tool as claimed in claim 8 wherein said stem is threadable in said sleeve.

* * * * *